US012676211B2

(12) United States Patent
Mistry et al.

(10) Patent No.: US 12,676,211 B2
(45) Date of Patent: Jul. 7, 2026

(54) SYSTEM, METHOD, AND MEDIUM FOR END TO END NMR BASED CRUDE PLANT OPTIMIZATION

(71) Applicant: Suncor Energy Inc., Calgary (CA)

(72) Inventors: Shashikant Mistry, Niagara-on-the-Lake (CA); Nathaniel Peters, Calgary (CA)

(73) Assignee: Suncor Energy Inc., Calgary (CA)

( * ) Notice: Subject to any disclaimer, the term of this patent is extended or adjusted under 35 U.S.C. 154(b) by 952 days.

(21) Appl. No.: 17/955,644

(22) Filed: Sep. 29, 2022

(65) Prior Publication Data

US 2024/0112761 A1    Apr. 4, 2024

(51) Int. Cl.
| | |
|---|---|
| *G16C 20/10* | (2019.01) |
| *C10G 7/06* | (2006.01) |
| *C10G 7/12* | (2006.01) |
| *G01N 24/08* | (2006.01) |
| *G16C 20/70* | (2019.01) |

(52) U.S. Cl.
CPC ............... *G16C 20/10* (2019.02); *C10G 7/06* (2013.01); *C10G 7/12* (2013.01); *G01N 24/085* (2013.01); *G16C 20/70* (2019.02)

(58) Field of Classification Search
CPC .......... G16C 20/10; G16C 20/70; C10G 7/06; C10G 7/12; G01N 24/085; G01N 24/081
See application file for complete search history.

(56) References Cited

U.S. PATENT DOCUMENTS

| | | | |
|---|---|---|---|
| 9,429,556 B2 | 8/2016 | Koseoglu | |
| 9,846,147 B2 | 12/2017 | Kumar et al. | |
| 10,175,661 B2 | 1/2019 | Trygstad | |
| 2018/0011037 A1* | 1/2018 | Koseoglu | ........... G01R 33/4625 |
| 2018/0216016 A1* | 8/2018 | Bakas | .................. B01J 19/0006 |

FOREIGN PATENT DOCUMENTS

| | | |
|---|---|---|
| CA | 2480104 C | 1/2011 |
| CA | 2963862 A1 | 6/2016 |
| CN | 103713604 A | 4/2014 |
| WO | 2017/023795 A1 | 2/2017 |

* cited by examiner

*Primary Examiner* — Prem C Singh
*Assistant Examiner* — Juan C Valencia
(74) *Attorney, Agent, or Firm* — Knobbe, Martens, Olson & Bear, LLP

(57)    ABSTRACT

There are provided systems, methods, and processor-readable media for optimizing the end to end operation of a hydrocarbon processing system using NMR spectroscopy data. The hydrocarbon processing system is configured to process hydrocarbon feedstock material, via a configuration defined by a set of configuration parameters, such that one or more final products are produced. A yield prediction model is used to process NMR data obtained from an NMR scan of the feedstock material to generate yield prediction data. The yield prediction data includes predictions of product yields of various intermediate products and/or final products. An optimization module is used to process the yield prediction data predicted by the trained yield prediction model such that optimized configuration parameter data is obtained. The optimized configuration parameter data is effective for establishing an optimized configuration for operating the hydrocarbon processing system that optimizes or improves an objective metric.

21 Claims, 7 Drawing Sheets

500

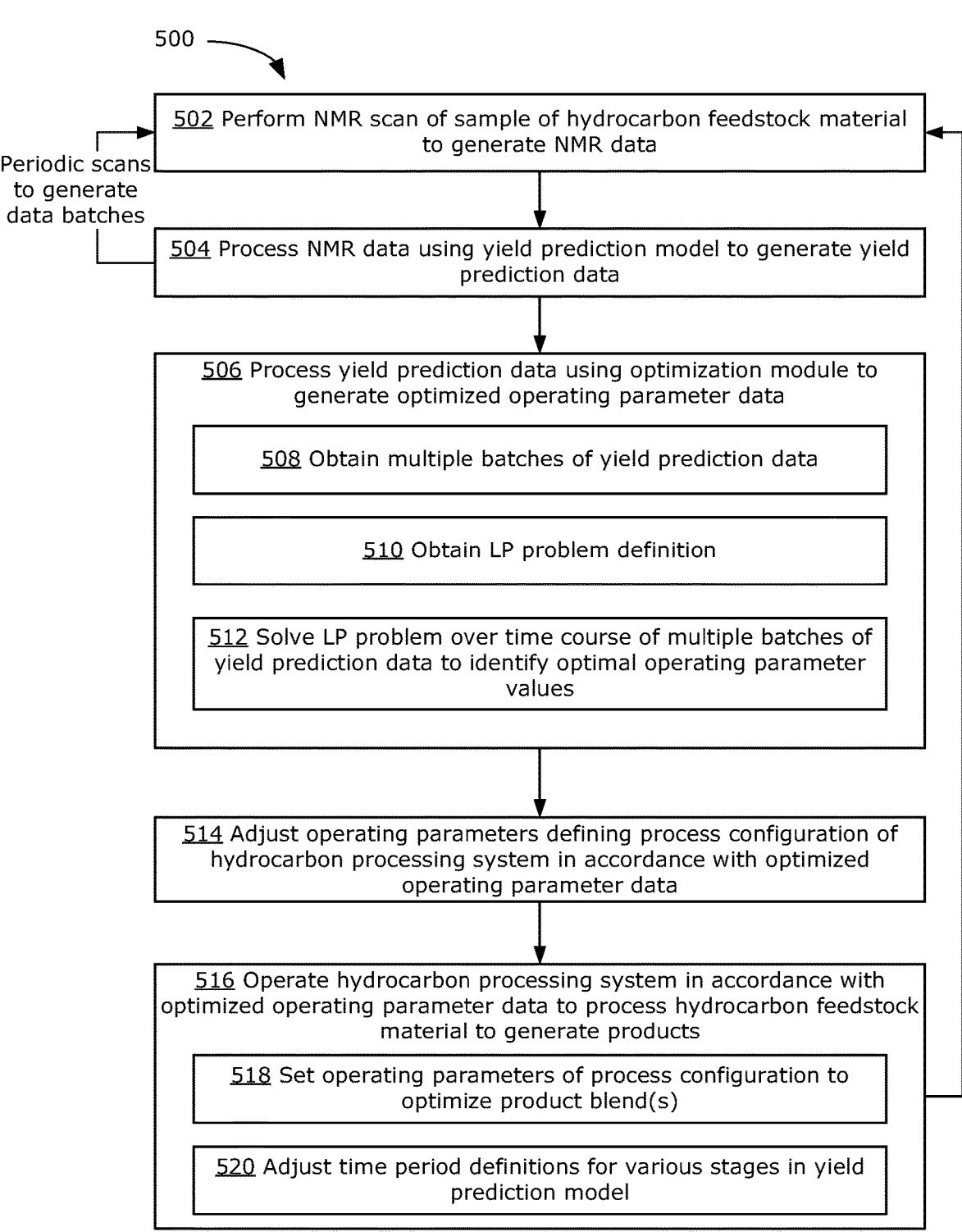

Periodic scans
to generate
data batches

502 Perform NMR scan of sample of hydrocarbon feedstock material to generate NMR data

504 Process NMR data using yield prediction model to generate yield prediction data

506 Process yield prediction data using optimization module to generate optimized operating parameter data

508 Obtain multiple batches of yield prediction data

510 Obtain LP problem definition

512 Solve LP problem over time course of multiple batches of yield prediction data to identify optimal operating parameter values

514 Adjust operating parameters defining process configuration of hydrocarbon processing system in accordance with optimized operating parameter data

516 Operate hydrocarbon processing system in accordance with optimized operating parameter data to process hydrocarbon feedstock material to generate products

518 Set operating parameters of process configuration to optimize product blend(s)

520 Adjust time period definitions for various stages in yield prediction model

FIG. 5

SYSTEM, METHOD, AND MEDIUM FOR END TO END NMR BASED CRUDE PLANT OPTIMIZATION

FIELD

The present disclosure relates to optimizing the processing of hydrocarbon materials, and in particular to systems, methods, and processor-readable media for optimizing the end to end operation of a crude oil processing system based on crude analysis using nuclear magnetic resonance spectroscopy.

BACKGROUND

Hydrocarbon material processing plants typically include processes for processing hydrocarbon feedstock materials to obtain enriched hydrocarbon products. These processes can include various chemical, mechanical, thermal, and/or other types of treatment of the feedstock materials in order to separate, isolate, synthesize, or otherwise obtain the enriched hydrocarbon products. The effectiveness of these processes can vary based on characteristics of the feedstock materials and/or based on process conditions, resulting in varying quantities and/or qualities of enriched hydrocarbon product from a given portion of feedstock material.

Skilled operators of processing plants can, over time, learn that certain configurations of these processes result in improved quantity and/or quality of enriched hydrocarbon product in the presence of certain feedstock characteristics or certain process conditions. However, the number of variables that can potentially affect the relationship between hydrocarbon characteristics, process conditions, and the quantity and quality of enriched hydrocarbon product produced, as well as the difficulty of directly ascertaining these variables, necessarily makes such human-based decisions crude and highly approximate, and operators are forced to rely upon broad heuristics in configuring these processes.

In the context of crude oil processing plants, such as crude refineries, the feedstock characteristics can be determined by performing various tests prior to or during processing. Nuclear Magnetic Resonance (NMR) spectroscopy can be used to analyze crude feedstock prior to processing in a refinery or production plant. This analysis can be used to determine properties of a sample of crude. However, this analysis is typically limited to determining the concentration of various components of the crude. This limits the usefulness of the analysis results.

Some efforts have been made to use NMR spectroscopy data to optimize operation of crude refining facilities. Unites States Patent Application Publication No. 2018/0216016 A1, entitled "SYSTEM AND METHOD OF PREDICTIVE ANALYTICS FOR DYNAMIC CONTROL OF A HYDROCARBON REFINING PROCESS", discloses a software-based system for predicting various parameters relevant to the operation of a desalter process in a crude refinery based on an NMR fingerprint of the crude feedstock being processed. It is suggested that the predicted parameters could be used as a basis for adjusting operations of the desalter process to achieve a specific objective, such as mitigating the formation of hydrochloric acid in the desalter process. However, the disclosure has several limitations. It is limited to optimizing a desalter process of a crude refinery, and provides little or no detail as to how other processes of a refinery can be modeled or optimized. The predictive models described in the disclosure are unspecified as to how they are constructed or configured. Furthermore, the disclosure only describes using the optimization process to achieve a single objective, such as mitigating the formation of hydrochloric acid.

Accordingly, it would be useful to provide techniques for optimizing the configuration of processes for processing feedstock material to obtain enriched hydrocarbon product that overcome one or more of the limitations identified above.

SUMMARY

The present disclosure describes systems, methods, and processor-readable media for optimizing the end to end operation of a hydrocarbon processing system using NMR spectroscopy data. The hydrocarbon processing system is configured to process hydrocarbon feedstock material, via a process configuration defined by a set of configuration parameters, such that one or more final products are produced. A yield prediction model is used to process NMR data obtained from an NMR scan of the feedstock material to generate yield prediction data. The yield prediction data includes predictions of product yields, such as rates or volumes of production of various intermediate products and/or final products. An optimization module is used to process the yield prediction data predicted by the trained yield prediction model such that optimized configuration parameter data is obtained. The optimized configuration parameter data is effective for establishing an optimized process configuration for operating the hydrocarbon processing system that optimizes or improves an objective metric.

In some embodiments, the trained yield prediction model receives as input not only the NMR data but also one or more other parameters relating to either feedstock characteristics of the feedstock material or process characteristics of the process configuration. In some embodiments, the yield prediction data generated by the trained yield prediction model comprises one or more product yields for each of a plurality of process units within the hydrocarbon processing system, wherein the predicted one or more product yields for each process unit are associated with a respective time period to which the prediction pertains. Thus, the trained yield prediction model can be effective to predict an end-to-end time course for the feedstock material and its derivatives through the entire hydrocarbon processing system, enabling the end-to-end optimization of the entire hydrocarbon processing system to optimize the objective metric.

In some embodiments, the optimization module solves a linear programming (LP) problem to optimize the objective metric, wherein the LP problem is defined by at least the objective metric and one or more constraints. In some embodiments, the objective metric comprises an objective function, defined as a function of the inputs to the optimization module. The constraints can define limits on operation of the hydrocarbon processing system, such as safety requirements, resource availability limits, etc. In some embodiments, the inputs to the optimization module include not only the yield prediction data predicted by the trained yield prediction model, but also at least a subset of the one or more other parameters used as inputs to the trained yield prediction model, i.e. the parameters relating to either feedstock characteristics of the feedstock material or process characteristics of the process configuration. Thus, the optimization module can provide a mechanism whereby multiple requirements (e.g., constraints) and objectives (e.g. positive and negative outcomes weighted based on their desirability) can be satisfied by the recommended process parameter information defining the optimal process configuration.

In the present disclosure, the term "objective metric" refers to a quantified metric defining a desired objective for the operator of a hydrocarbon processing system. In some contexts, an objective metric can be a numerical function calculated based on the values of various input parameters. An objective metric can model or correspond to a desired objective or weighted combination of objectives, such as revenue, profit, efficiency, product throughput, environmental impact, fulfillment of demand, etc. Unless otherwise indicated, a high value of an objective metric as described herein indicates a more fully satisfied objective: an "improved" objective metric can therefore refer to an increased objective metric, and an "optimal" or "optimized" objective metric can refer to a maximized objective metric.

In the present disclosure, the term "profit" refers to revenue net costs. Thus, a profit can be negative.

In the present disclosure, the term "product" refers to either an intermediate product or a final product of a hydrocarbon processing system.

In the present disclosure, the terms "yield" or "product yield" refer to a measure of an amount of a product generated or synthesized by a hydrocarbon processing system or a component or stage thereof. A yield may be a rate of production, such as barrels per hour, a gross volume of production, such as barrels, or another measure of an amount of product generated.

As used herein, statements that a second item (e.g., a signal, value, scalar, vector, matrix, calculation, or bit sequence) is "based on" a first item can mean that characteristics of the second item are affected or determined at least in part by characteristics of the first item. The first item can be considered an input to an operation or calculation, or a series of operations or calculations, that produces the second item as an output that is not independent from the first item.

In some aspects, the present disclosure describes a method. A nuclear magnetic resonance (NMR) scan of a sample of a hydrocarbon feedstock material is performed to generate NMR data. The NMR data is processed, using a yield prediction model, to generate yield prediction data. The yield prediction data includes a predicted yield for each of a plurality of products resulting from the processing of the hydrocarbon feedstock material by a hydrocarbon processing system.

In some aspects, the present disclosure describes a system. The system comprises a nuclear magnetic resonance (NMR) spectroscopy scanner for performing NMR scans of hydrocarbon feedstock material, a processor device, and a memory storing instructions that, when executed by the processor device, cause the system to perform a number of operations. A nuclear magnetic resonance (NMR) scan of a sample of a hydrocarbon feedstock material is performed to generate NMR data. The NMR data is processed, using a yield prediction model, to generate yield prediction data. The yield prediction data includes a predicted yield for each of a plurality of products resulting from the processing of the hydrocarbon feedstock material by a hydrocarbon processing system.

In some examples, the method further comprises adjusting one or more operating parameters defining a process configuration of the hydrocarbon processing system based on the yield prediction data.

In some examples, the hydrocarbon feedstock material comprises crude oil, and the plurality of products includes at least one of the following: a naphtha product, a distillate product, a gas oil product, a crude bottom product, a light vacuum gas oil product, a heavy vacuum gas oil product, and a coker feed product.

In some examples, the plurality of products comprises a naphtha product. The method further comprises adjusting one or more operating parameters of the process configuration, based on the yield prediction data, to maintain a predicted pressure of at least one stage of the hydrocarbon processing system below a pressure threshold.

In some examples, the yield prediction data includes, for each respective stage of a plurality of stages of the hydrocarbon processing system, a predicted yield of at least one respective product at a respective time period, such that the respective time period corresponds to a time at which the hydrocarbon feedstock material or materials derived from the hydrocarbon feedstock material are being processed by the respective stage.

In some examples, the method further comprises repeating, for one or more batches of hydrocarbon feedstock material, the steps of performing the NMR scan and generating the yield prediction data, such that yield prediction data is obtained for a plurality of batches of hydrocarbon feedstock material. The yield prediction data for the plurality of batches of hydrocarbon feedstock material is processed to determine end to end product yield data comprising predicted yields for at least one product over at least one time period for each stage. One or more operating parameters of the process configuration are adjusted based on the end to end product yield data.

In some examples, adjusting the one or more operating parameters of the hydrocarbon processing system based on the end to end product yield data comprises a number of operations. A linear programming (LP) problem definition comprising an objective function is obtained. The end to end product yield data is processed, using an optimization module comprising an LP problem solver, to solve a LP problem defined by the LP problem definition, thereby generating optimized operating parameter data comprising one or more values for the operating parameters corresponding to a desired value for the objective function. The one or more operating parameters are adjusted based on the optimized operating parameter data.

In some examples, the objective function includes a plurality of terms corresponding to market prices for a plurality of final products producible by the hydrocarbon processing system.

In some examples, the LP problem definition further comprises one or more constraints.

In some examples, the one or more constraints includes a pressure constraint representative of maintaining a pressure value below a pressure threshold at a naptha processing stage of the hydrocarbon processing system. The pressure value is predicted based on a predicted rate of production of a naptha product of the yield prediction data.

In some examples, adjusting the one or more operating parameters based on the optimized operating parameter data comprises adjusting the one or more operating parameters to maintain the pressure value below the pressure threshold at the naptha processing stage.

In some examples, the one or more constraints includes a product supply constraint representative of a commitment to supply a committed quantity of a first product.

In some examples, the operating parameters include one or more parameters representative of at least one of the following: a temperature, a flow rate, a dwell time, and a valve position.

In some examples, the method further comprises, after adjusting the operating parameters defining the process configuration: processing the hydrocarbon feedstock material, using the hydrocarbon processing system configured in accordance with the process configuration, to generate the plurality of products.

In some examples, the yield prediction model generates the yield prediction data by processing the NMR data and one or more additional parameters. The one or more additional parameters comprise at least one of the following: one or more process characteristics representative of characteristics of the hydrocarbon processing system, and one or more feedstock characteristics representative of characteristics of the hydrocarbon feedstock material.

In some examples, the yield prediction model is a machine learning model trained using supervised learning based on training data. The training data comprises NMR data for a plurality of hydrocarbon feedstock material batches, and yield data representative of, for each hydrocarbon feedstock material batch, a plurality of product yields generated by processing the hydrocarbon feedstock material batch via the hydrocarbon processing system.

In some examples, the yield prediction model is a statistical model generated based on statistical correlations between: NMR data for a plurality of hydrocarbon feedstock material batches, and yield data representative of, for each hydrocarbon feedstock material batch, a plurality of product yields generated by processing the hydrocarbon feedstock material batch via the hydrocarbon processing system.

In some examples, the NMR data comprises a NMR fingerprint.

In some examples, the NMR data is representative of a composition of the sample, comprising a plurality of components each associated with a respective concentration.

In some aspects, the present disclosure describes a system. The system comprises a nuclear magnetic resonance (NMR) spectroscopy scanner for performing NMR scans of hydrocarbon feedstock material, a processor device, and a memory storing instructions that, when executed by the processor device, cause the system to perform one or more of the methods described above.

In some aspects, the present disclosure describes a non-transitory computer-readable medium storing instructions thereon to be executed by a processor device, the instructions, when executed, causing the processor device to perform one or more of the methods described above.

BRIEF DESCRIPTION OF THE DRAWINGS

Reference will now be made, by way of example, to the accompanying drawings which show example implementations of the present application, and in which:

FIG. 5 is a flowchart showing operations of a method for optimizing the end to end operation of a hydrocarbon processing system using nuclear magnetic resonance spectroscopy data, in accordance with example implementations described herein.

Similar reference numerals can have been used in different figures to denote similar components.

DESCRIPTION OF EXAMPLE
IMPLEMENTATIONS

The present disclosure describes systems, methods, and processor-readable media for optimizing the end to end operation of a hydrocarbon processing system using nuclear magnetic resonance spectroscopy data.

Figure 1:
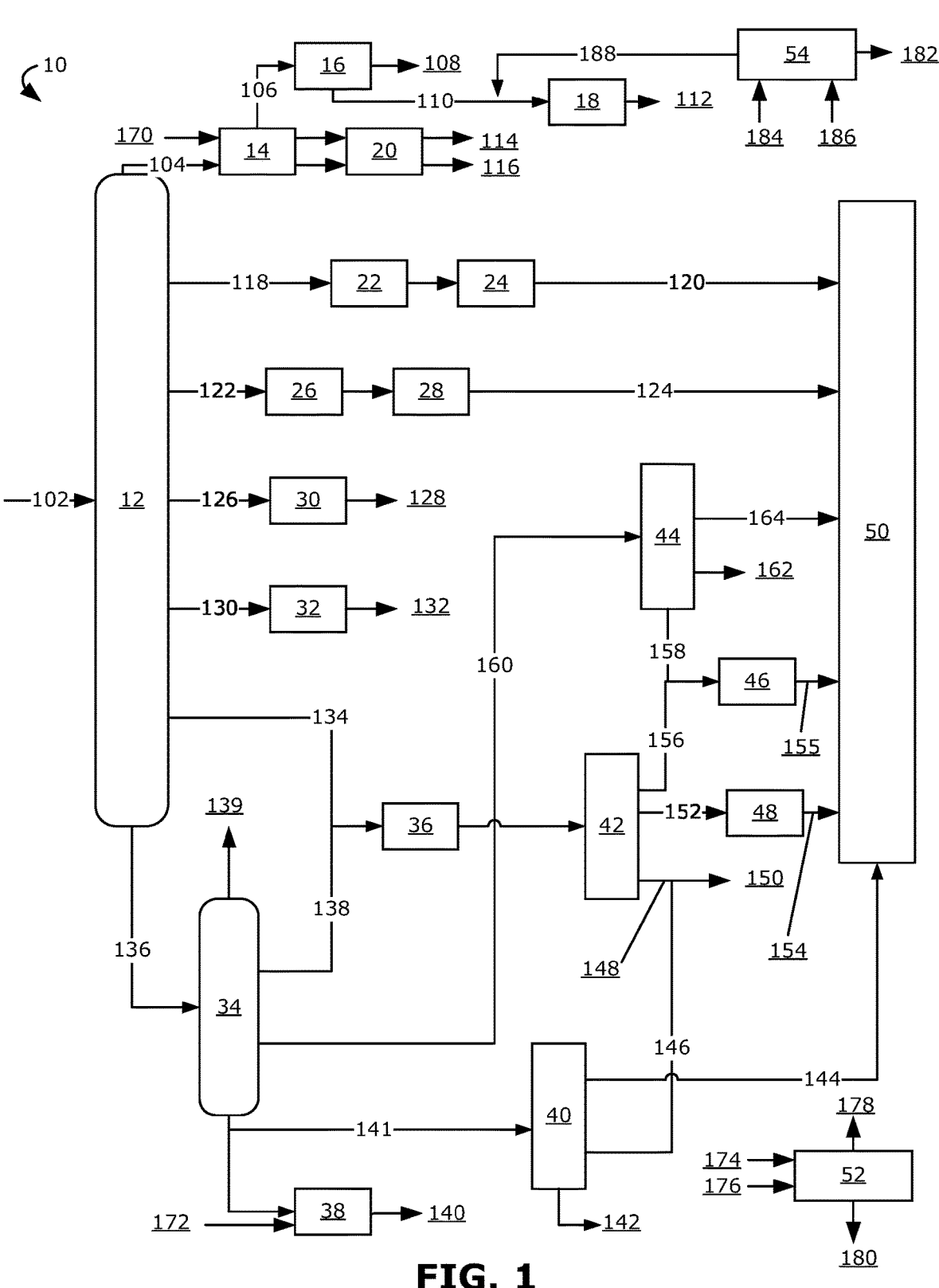
FIG. 1 is a block diagram showing the stages of a hydrocarbon processing system suitable for implementation of examples described herein.

FIG. 1 is a block diagram of an example hydrocarbon processing system 10, shown as a crude oil processing system. An incoming batch of hydrocarbon feedstock material, in this case a batch of crude 102, is processed by the hydrocarbon processing system 10 to produce several final products, described in detail below. The hydrocarbon processing system 10 includes a number of stages, each shown as a separate process unit and described below. The stages of the hydrocarbon processing system 10 define one or more processes, conducted under defined process conditions, via which the crude 102 is converted to intermediate or final products. Each one of the one or more processes, independently, is effectuated via a respective one or more unit operations. The unit operations are co-operatively coupled for effecting production of the final products. The unit operations can include one or more of mixing, separation, heating, cooling, and chemical reaction. Each one of the unit operations include one or more material inputs and one or more product outputs.

The process conditions of each unit operation, i.e. each stage, can be defined by a set of parameters referred to herein as process characteristics. Some process characteristics can be controlled by an operator of the hydrocarbon processing system 10, and can be referred to herein as operating parameters. Adjustment of an operating parameter can include adjustment of actual physical conditions of a process within the hydrocarbon processing system 10, through various physical adjustment means, such as actuating valves, modulating the amount of energy supplied to a heating element, instructing personnel to increase or decrease an amount of chemical additive manually added to a stage, etc.

Other process characteristics can be measured (e.g., by sensors), but not directly controlled. These parameters can be referred to as process measurements. In some examples, a parameter can be both measurable and controllable, such as a temperature of a stage measured and controlled by a thermometer and thermostat, and can thereby be regarded as both a process measurement and an operating parameter.

In addition to the process characteristics described above, the products produced at each stage can be affected by a further set of parameters, referred to herein as feedstock characteristics. Feedstock characteristics represent physical characteristics of the hydrocarbon feedstock material (such as crude 102) being processed by a stage of the hydrocarbon processing system 10 at a given point in time. In examples described herein, feedstock characteristics of an incoming batch of hydrocarbon feedstock material can be determined at least in part based on NMR data generated by an NMR scan, i.e. by NMR spectroscopy.

The stages of the hydrocarbon processing system 10 will now be described briefly. It will be appreciated that the stages shown in FIG. 1 are functional units that can include many sub-components such as pumps, heaters, and other equipment not fully described herein.

An atmospheric distillation unit 12 operates as a distillation column to perform atmospheric distillation of the incoming crude 102 into several products, including gas (i.e. natural gas) 104, light naptha 118, heavy naptha 122, unrefined jet fuel or kerosene 126, wet diesel oil 130, atmospheric gas oil 134, and atmospheric bottoms 136. In some examples, the batch of crude feedstock 102 can be desalted by a desalter and/or heated by a heater prior to arriving at the atmospheric distillation unit 12.

The gas 104 is mixed with other gases 170 produced by other stages and processed by a gas processing unit 14, producing fuel gas 106 as well as liquefied petroleum gas (LPG) and butane streams. The LPG and butane streams are processed by a merox (mercaptan oxidation) treater unit 20 to generate the final products LPG 114 and butanes 116. The fuel gas 106 is processed by an amine treatment unit 16 to separate out hydrogen sulfide ($H_2S$) 110, generating refinery fuel 108. The $H_2S$ 110 is mixed with $H_2S$ 188 from the sour water stripper (described below) and the mixed $H_2S$ is processed by a Claus sulfur plant 18 applying a Claus process to generate sulfur 112, which can be regarded as another final product of the hydrocarbon processing system 10.

The other products generated by the atmospheric distillation unit 12 are processed by their own respective chains of process units. The light naptha 118 is processed by a hydrotreater unit 22, and its output is processed by an isomerization plant unit 24, thereby generating an isomerate 120, which is provided to a gasoline blending pool 50 for generating gasoline having a blend of different intermediate products of the hydrocarbon processing system 10. The hydrotreater unit 22 and isomerization plant unit 24, like a number of other units described herein (22, 24, 26, 28, 32, 36, 44, 48), each receives a hydrogen ($H_2$) and a gas output, neither of which is shown in FIG. 1 for the sake of visual simplicity. The gas output of each such unit is channeled into the other gases 170 described above.

Similarly, the heavy naptha 122 is processed by a hydrotreater unit 26 followed by a catalytic reformer unit 28, thereby generating reformate 124, which is also provided to the gasoline blending pool 50.

The unrefined jet fuel or kerosene 126 is treated by a further merox treater unit 30 to generate a final product of jet fuel or kerosene 128. Similarly, the wet diesel oil 130 is treated by a hydrotreater unit 32 to generate a final product of diesel oil 132.

The atmospheric bottoms 136 undergo further distillation at a vacuum distillation unit 34, which separates them into several products: evacuated non-condensibles 139, light vacuum gas oil 138, heavy vacuum gas oil 160, and the vacuum residuum 141. The light vacuum gas oil 138 is mixed with the atmospheric gas oil 134 from the atmospheric distillation unit 12 and provided to a FCC (fluid catalytic cracker) feed hydrotreater unit 36 before proceeding to the FCC unit 42, described below. The heavy vacuum gas oil 160 is processed by a hydrocracker unit 44, described below. A portion of the vacuum residuum 141 is processed by a delayed coker unit 40, described below; the remaining portion is provided to an asphalt blowing unit 38, which applies an input feed of air 172 to generate a final product of asphalt 140.

The hydrocracker unit 44, FCC unit 42, and delayed coker unit 40 produce a number of products, some of which are used as final products, others of which are provided to the gasoline blending pool 50 as-is or after further processing. The hydrocracker unit 44 generates hydrocracked gasoline 164, final product diesel oil 162, and i-butane 158. The hydrocracked gasoline 164 is provided to the gasoline blending pool 50. The i-butane 158 is provided to an alkylation unit 46, described below.

The FCC unit 42 has a gas input (not shown) which is channeled to the other gases 170. The FCC unit 42 generates butenes and pentenes 156, naptha 152, and FCC gas oil 148. The butenes and pentenes 156 are provided as a further input to the alkylation unit 46, which generates alkylate 155, which is provided to the gasoline blending pool 50. The alkylation unit 46 also has a gas input (not shown) which is channeled to the other gases 170.

The naptha 152 is hydrotreated by a hydrotreater unit 48, generating FCC gasoline 154 which is provided to the gasoline blending pool 50. The FCC gas oil 148 is mixed with coker gas oil 146 from the delayed coker unit 40 (described below) to generate a final product of fuel oil 150.

The delayed coker unit 40 generates coker naptha 144, which can be hydrotreated and reformed (not shown) before being provided to the gasoline blending pool 50. The delayed coker unit 40 also generates coker gas oil 146, described above. The delayed coker unit 40 also generates a final product of petroleum coke 142.

Sour waters can be generated by the various stages of the hydrocarbon processing system 10, including waters contaminated by ammonia ($NH_3$) and/or hydrogen sulfide ($H_2S$). These sour waters 186 are provided to a sour water steam stripper unit 54 along with steam 184 to generate stripped water 182 as well as the $H_2S$ 188 described above.

The hydrogen used by various stages of the hydrocarbon processing system 10 can be generated by a hydrogen synthesis unit 52, which takes natural gas 174 and steam 176 as inputs and generates $CO_2$ 178 and $H_2$ 180.

The final products of the hydrocarbon processing system 10 are those identified above, as well as the gasoline blend generated by the gasoline blending pool 50. These final products, as well as all intermediate products described above, can jointly form the set of products generated by the stages of the hydrocarbon processing system 10. Some embodiments described herein are effective to predict and optimize production, such as a rate of production or a gross yield (e.g., number of barrels), of one or more of the products to achieve desired objectives, based on feedstock characteristics of the hydrocarbon feedstock material (e.g., crude 102) determined at least in part by a NMR scan.

An NMR scanner 402 (no shown) may be used to scan incoming hydrocarbon feedstock material (e.g., crude 102). In some embodiments, the NMR scanner is a conventional, commercially available NMR analyzer such as an AI-60 NMR with a 5 mm 1H probe, marketed by Aspect Imaging™.

In some embodiments, for example, the processing performed by the hydrocarbon processing system 10 enables the collection of data for purposes of training a yield prediction model 302. A computing system (such as computing system 240, described below with reference to FIG. 2) can be used to obtain yield prediction data 322. In some examples, the computing system can also be used to obtain additional parameter data 310 including one or more feedstock parameters 312 and/or process parameters 314.

Figure 2:
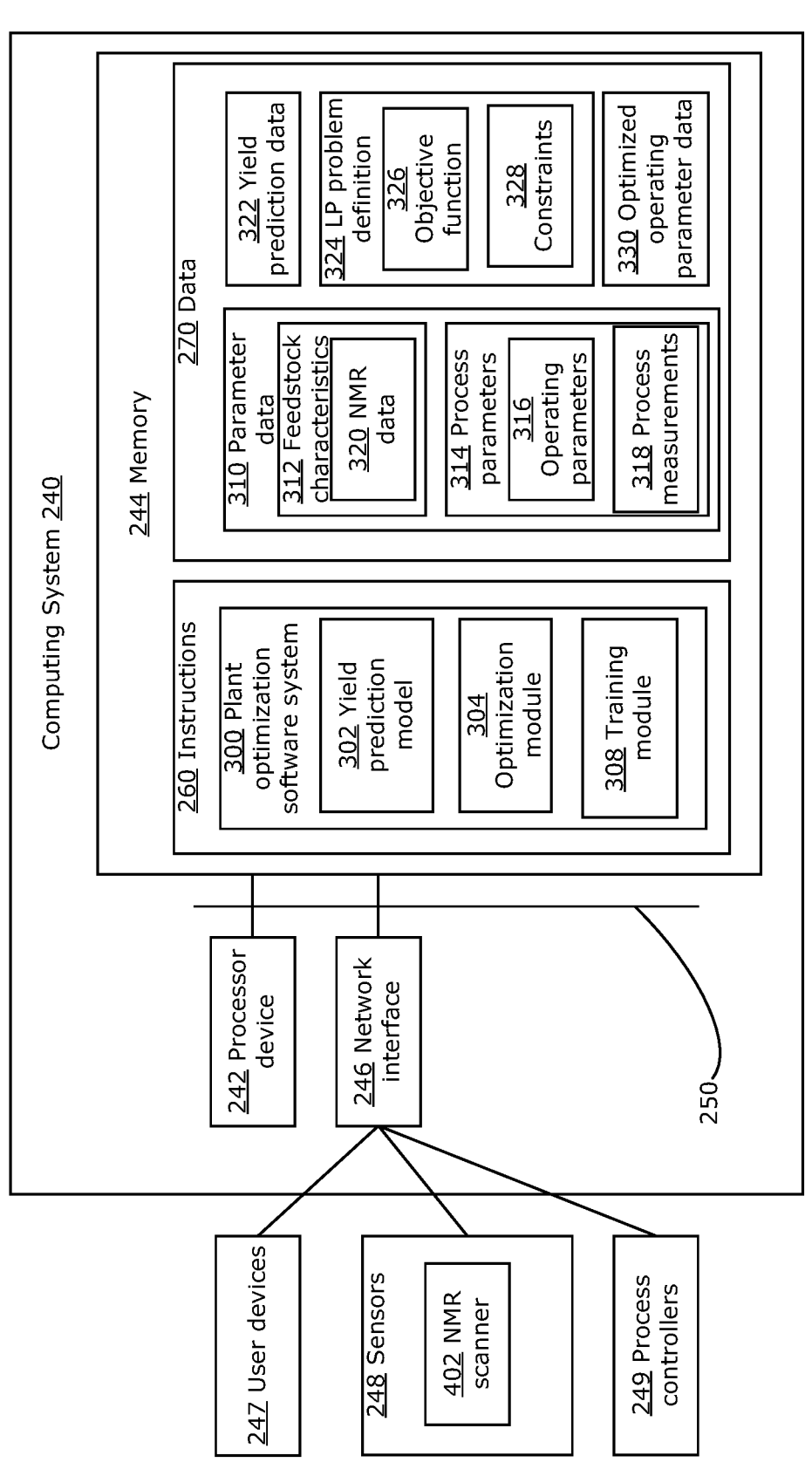
FIG. 2 is a block diagram of an example computing system suitable for implementation of examples described herein.

FIG. 2 is a block diagram of an example computing system 240 including computing hardware suitable for processing hydrocarbon feedstock material and optimizing the operation of a hydrocarbon processing system 10 according to example embodiments described herein. In some implementations, computing system 240 can be an electronic computing device, such as a networked server. In other implementations, the computing system 240 can be a distributed computing system including multiple devices (such as a cloud computing platform) or a virtual machine running on one or more devices in mutual communication over a network. Other examples suitable for implementing implementations described in the present disclosure can be used, which can include components different from those discussed below. Although FIG. 2 shows a single instance of each component, there can be multiple instances of each component in the computing system 240.

The computing system 240 can include one or more processor devices (collectively referred to as processor device 242 or processor 242). The processor device 242 can include one or more processor devices such as a processor, a microprocessor, a digital signal processor, an application-specific integrated circuit (ASIC), a field-programmable gate array (FPGA), a dedicated logic circuitry, a dedicated artificial intelligence processor unit, or combinations thereof.

The computing system 240 can include one or more network interfaces (collectively referred to as network interface 246) for wired or wireless communication over a network. The network interface 246 can include wired links (e.g., Ethernet cable) and/or wireless links (e.g., one or more antennas). The computing system 240 can communicate with one or more user devices 247 (such as user workstation computers) via the network interface 246. The computing system 240 can also communicate with various sensors 248 or other data sources to obtain data used in operating and optimizing the hydrocarbon processing system 10, such as sensors 248 or other data sources supplying feedstock characteristics and/or process characteristics. In some embodiments, the sensors 248 include an NMR scanner 402 for performing NMR spectroscopy on samples of the hydrocarbon feedstock material (e.g., crude 102) and thereby generating NMR data, such as a NMR fingerprint of the hydrocarbon feedstock material. The computing system 240 can also communicate with various process controllers 249 via the network interface 246 to control the operating parameters of the various components of the hydrocarbon processing system 10. In some examples, the user devices 247 and/or the components of the hydrocarbon processing system 10 can communicate with the computing system 240 through other means, such as an input/output interface of the computing system 240 (not shown) or through an intermediate device in communication with the computing system 240.

The computing system 240 can include one or more non-transitory memories (referred to collectively as a memory 244), which can include a volatile or non-volatile memory (e.g., a flash memory, a random access memory (RAM), and/or a read-only memory (ROM)). The memory 244 can also include one or more mass storage units, such as a solid state drive, a hard disk drive, a magnetic disk drive and/or an optical disk drive.

The memory 244 can store instructions for execution by the processor device 242 to carry out examples described in the present disclosure. The instructions can include instructions for implementing and operating the plant optimization software system 300 described below with reference to FIGS. 3A-3B. In some embodiments, the plant optimization software system 300 includes subsystems or functional modules such as a yield prediction model 302, an optimization module 304, and a training module 308, all described below with reference to FIGS. 3A-3B. The memory 244 can include other software instructions, such as for implementing NMR analyzer software for generating the NMR data 320 using the NMR scanner 402, an operating system, and other applications/functions. In some examples, the computing system 240 can additionally or alternatively execute instructions from an external memory (e.g., an external drive in wired or wireless communication with the computing system 240) or can be provided executable instructions by a transitory or non-transitory computer-readable medium. Examples of non-transitory computer readable media include a RAM, a ROM, an erasable programmable ROM (EPROM), an electrically erasable programmable ROM (EEPROM), a flash memory, a CD-ROM, or other portable memory storage.

The memory 244 can store data used by the plant optimization software system 300. Parameter data 310, such as feedstock characteristics 312 and process parameters 314, can be stored in the memory 244. In some examples, the feedstock characteristics 312 can include NMR data 320 generated by the NMR scanner 402, as well as additional feedstock characteristics 312 obtained from other sensors 248 or other data sources. The process parameters 314 can include operating parameters 316 obtained from the controllable operational settings of the various stages of the hydrocarbon processing system 10, as well as process measurements 318 obtained from various sensors 248 located at the various stages. In some embodiments, the process measurements 318 can include yield data 340 (described with reference to FIG. 3A below) representative of actual yields of one or more intermediate or final products of the hydrocarbon processing system 10. In some examples, data sources used to generate feedstock characteristics 312 and/or process measurements 318 can include laboratory testing of one or more of the materials processed or generated by the hydrocarbon processing system 10, such as the hydrocarbon feedstock material 102 and/or one or more intermediate or final products.

Various subsystems of the plant optimization software system 300 can generate or use additional data 270, which can be stored in the memory 244. The yield prediction model 302 can generate yield prediction data 322. In some embodiments, the optimization module 304 can optimize operation of the hydrocarbon processing system 10 according to a linear programming (LP) problem definition 324, which can include an objective function 326 and one or more constraints 328. The output of the optimization module 304 can be optimized operating parameter data 330, representative of a solution to the LP problem defined by the LP problem definition 324, and effective to define a set of values for the operating parameters 316 of a process configuration of the hydrocarbon processing system 10 that achieves a desired goal defined by the objective function 326 and/or constraints 328.

The computing system 240 can also include a bus 250 providing communication among components of the computing system 240, including those components discussed above. The bus 250 can be any suitable bus architecture including, for example, a memory bus, a peripheral bus or a video bus, or the bus 250 can be another communication link such as a network interface 246.

Figure 3A:
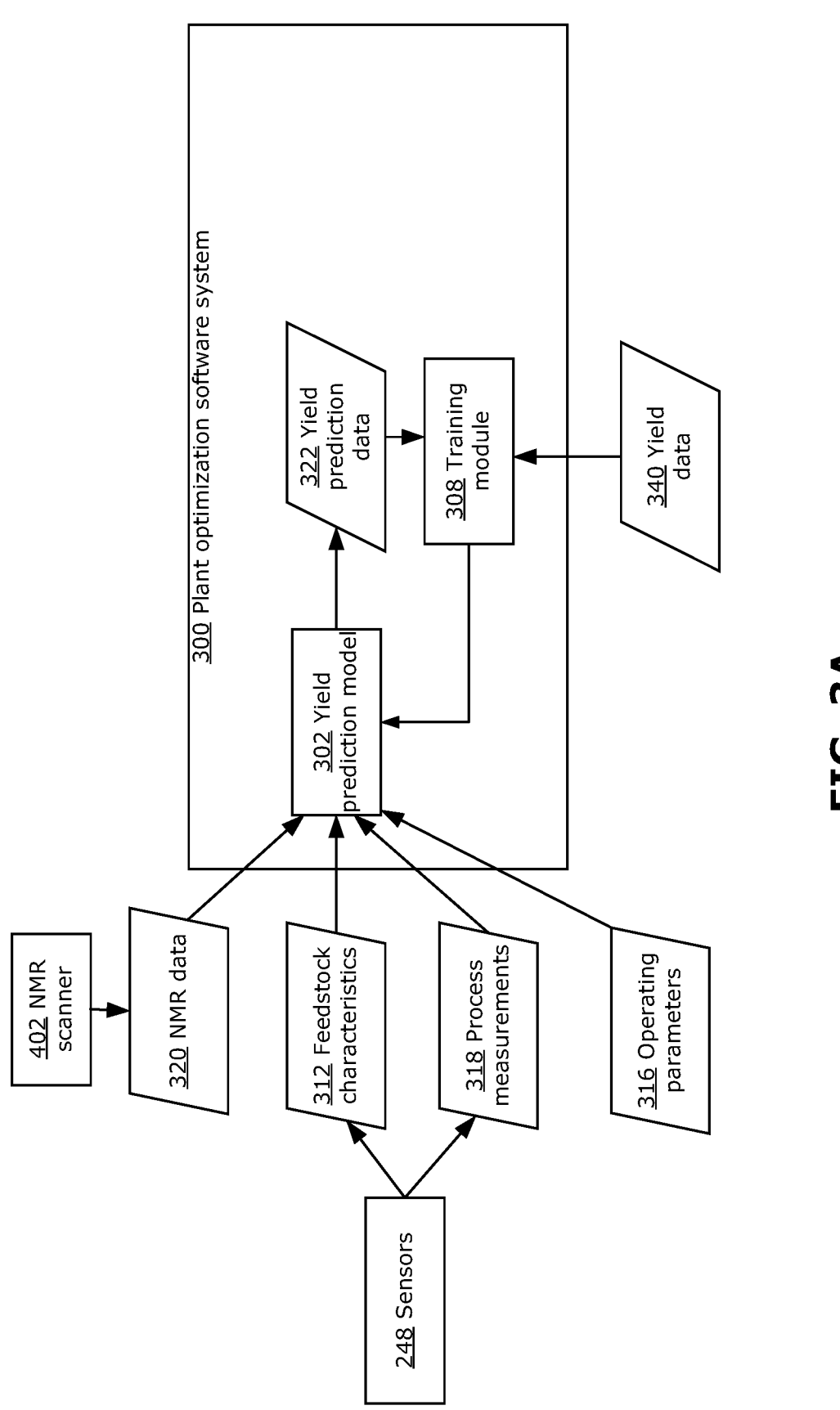
FIG. 3A is a block diagram of an example plant optimization software system operating in a training mode, in accordance with example implementations described herein.
Figure 3B:
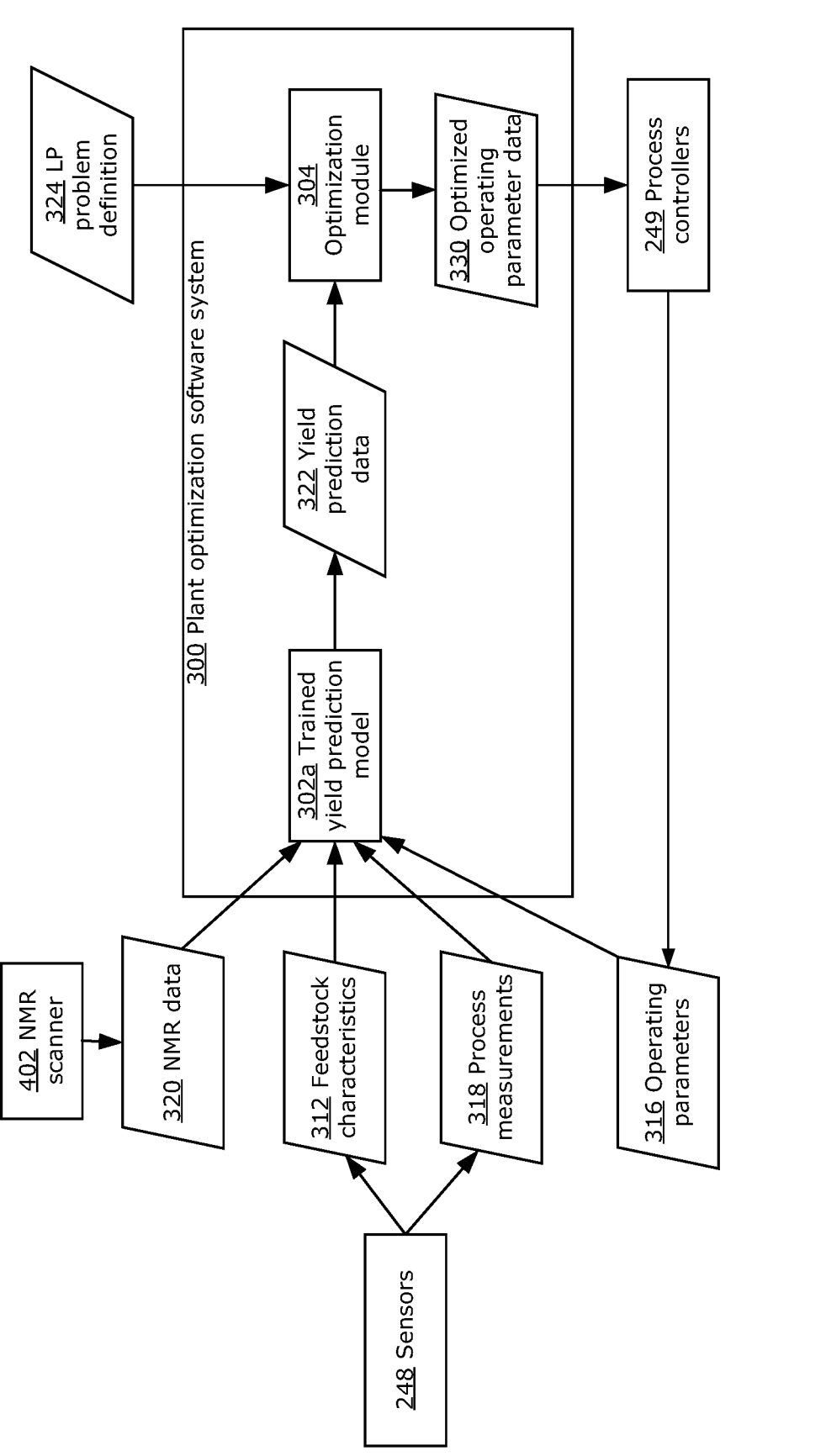
FIG. 3B is a block diagram of an example plant optimization software system operating in a deployment mode, in accordance with example implementations described herein.

FIGS. 3A-3B illustrate an example plant optimization software system 300. The plant optimization software system 300 is executed by a computing system 240 to perform the methods and operations described herein. The plant optimization software system 300 includes a number of functional modules or subsystems 302, 304, 306, as described below. It will be appreciated that some implementations can omit one or more of the described subsystems and/or can combine the functions of two or more of the described subsystems into a single component. In some implementations, different functions of the plant optimization software system 300 can be performed on different devices other than the computing system 240. For example, computationally intensive functions such as training machine learning models and executing trained machine learning models can be performed on a cloud computing platform in communication with a local computing system 240.

In some implementations, the plant optimization software system 300 operates to predict and/or optimize product yields of the hydrocarbon processing system 10. It will be appreciated that similar plant optimization software systems 300 could be configured, trained, and deployed to optimize the operation of different type of hydrocarbon processing system 10 from the crude refinery shown in FIG. 1.

FIG. 3A shows the plant optimization software system 300 operating in a training mode in order to train the yield prediction model 302 used by the plant optimization software system 300. The plant optimization software system 300 includes a yield prediction model 302 which must be trained using machine learning algorithms before the plant optimization software system 300 can be executed to monitor and/or optimize the operation of the hydrocarbon processing system 10 in a deployment mode (as shown in FIG. 3B).

During training mode, the ore processing module 310 uses a prediction model training submodule 308 to train the yield prediction model 302. A training dataset, consisting of training data 326, can be used to train the yield prediction model 302 using any of a number of machine learning techniques, such as supervised, unsupervised, or semi-supervised learning techniques. In some embodiments, the yield prediction model 302 includes an artificial neural network trained using supervised learning. In some embodiments, the yield prediction model 302 includes a statistical model trained using a genetic algorithm.

In some embodiments, the yield prediction model 302 includes an artificial neural network, which is trained by the training module 308 using back-propagation to generate a trained yield prediction model 302*a* (shown in FIG. 3B). The training mode shown in FIG. 3A uses a supervised learning algorithm to train the yield prediction model 302 using training data consisting of semantically labelled data samples. The data samples used as inputs to the yield prediction model 302 can include the various inputs shown on the left side of FIG. 3A: the NMR data 320, operating parameters 316, and optionally one or more additional parameters such as feedstock characteristics 312 and/or process measurements 318. The yield prediction model 302 processes the inputs to generate yield prediction data 322 representative of at least a predicted yield (e.g., rate of production or volume of production) for each of one or more intermediate and/or final products of the hydrocarbon processing system 10. In some examples, the yield prediction data 322 predicts the product yields for multiple stages of the hydrocarbon processing system 10 at respective periods of time corresponding to a time at which the respective stage is expected to process the current batch of hydrocarbon feedstock material, as described in greater detail below with reference to FIG. 4. In some examples, the yield prediction data 322 includes other predicted parameters, such as one or more predicted feedstock characteristics and/or process measurements. In some examples, the yield prediction data 322 predicts the one or more product yields and/or the one or more additional parameters for one or more stages of the hydrocarbon processing system 10, and the predictions for each stage correspond to a time period when that stage is predicted to be processing the hydrocarbon material batch (e.g. crude batch 102) or intermediate products derived therefrom, as described in greater detail below with reference to FIG. 4.

The training module 308 then compares the yield prediction data 322 to yield data 340 indicative of ground truth (i.e., actual) product yields for one or more intermediate and/or final products, applying a loss function in order to generate a loss. In some examples, in which the yield prediction data 322 also predicts one or more additional parameters, ground truth data for the additional parameters is also used in the comparison. The training module 308 propagates the loss backward through the yield prediction model 302 to adjust the learnable parameters of the yield prediction model 302 using gradient descent or other known machine learning techniques. Thus, the yield data 340 serves as semantic labels for the data samples (e.g., NMR data 320, operating parameters 316, feedstock characteristics 312, process measurements 318) used in training.

It will be appreciated that other types of models, trained using various machine learning techniques (also called "machine learning models"), can be used in some embodiments to implement the yield prediction model 302 and/or the optimization module 304 described below with reference to FIG. 3B.

In some embodiments, the NMR data 320 includes NMR spectroscopy data. In some embodiments, the NMR data 320 includes estimates of the composition of the scanned sample, based on laboratory testing data performed on historical samples of material. For example, prior to training the yield prediction model 302, NMR scans and laboratory testing can be performed on a set of hydrocarbon feedstock material samples, such as producing distillations for all components of each sample. The yields of distilled components and the NMR scans can then be used to generate NMR data 320 representing the actual composition of a sample as derived directly from the NMR scan. The yield prediction model 302 can then be trained, as described above, to predict yields from a sample having a definite composition (predicted directly from the NMR data 320), based on the other variables affecting actual yields (e.g., process measurements 318 and operating parameters 316). Thus, in some examples the feedstock characteristics 312 are not used as a separate set of data inputs but are instead derived from the NMR scan and laboratory testing and incorporated into the NMR data 320. For example, in some embodiments the NMR data 320 encodes a composition of the sample, consisting of a plurality of components (e.g., naptha, distillate, gas oil, bottoms), each component being associated with a respective concentration in the sample. Based on these concentrations of components in the sample (and therefore in the batch of hydrocarbon feedstock material), the prediction model 302 can predict the yields of the various products at various stages at various times. The list of products whose yields are predicted may or may not differ from the list of components represented in the NMR data 320: for example, if the NMR data 320 encodes percentages of four different components, the prediction model could predict yields of 10 different intermediate and final products at various stages at various times.

In some embodiments, the yield prediction model 302 is a statistical model constructed based on the laboratory testing, such as correlations between NMR scans and component distillations. In some examples, the yield prediction model 302 can estimate components of a scanned sample based on 90% boiling points for each component obtained during the distillation process. In embodiments using the yield prediction model 302 to predict the composition of the sampled batch of hydrocarbon feedstock material, the optimization module 304 (described below) can be used to obtain a desired blend of final products at a given time by adjusting the flow rates, temperatures, and other operating parameters 316 of the various stages such that the predicted components of the current batch of hydrocarbon feedstock material are converted into the various intermediate products and final products at the desired rates, and having the desired blends of components, as dictated by the goals of the optimization module 304 (such as the objective function 326 and constraints 328 described below).

FIG. 3B shows the operation of the plant optimization software system 300 in a deployment mode, after the yield prediction model 302 has completed training such that the yield prediction model 302 constitutes a trained yield prediction model 302A. In deployment mode, the plant optimization software system 300 is effective to monitor parameter information 310 and to optimize the processing of hydrocarbon feedstock material by adjusting the operating parameter values of the hydrocarbon processing system 10 accordingly. The optimization process performed by the plant optimization software system 300 in deployment mode can be performed in real time while the hydrocarbon feedstock material is being processed.

In deployment mode, the ore processing module 310 includes an optimization module 304. In some embodiments, the optimization module 304 uses a LP solver to optimize the operating parameters 316 of the process configuration, based on the predicted product yields and/or other predicted parameter values of the yield prediction data 322 generated by the trained yield prediction model 302a. The LP solver uses one or more known algorithms or techniques for deriving or approximating solutions to LP problems to generate optimized operating parameter data 330 comprising a set of parameter values for one or more of the operating parameters 316. When the operating parameters 316 of the hydrocarbon processing system 10 are adjusted by the process controllers 249 (and/or other means of controlling the operations of the hydrocarbon processing system 10) in accordance with the optimized operating parameter data 330, such that the various stages of the optimized operating parameter data 330 operate in accordance with the adjusted operating parameter values, the yields of the various products generated by one or more stages of the hydrocarbon processing system 10 will improve or optimize the objective function 326 while also satisfying the constraint 328 of the LP problem definition 324.

As described above, the LP problem definition 324 can include an objective function 326 and one or more constraints 328. In some examples, the objective function 326 includes terms that correspond to a profit to be maximized: for example, a set of yields for a set of final products can be multiplied by a current market price for each such final product, with associated costs subtracted (such as costs relating to storage, transportation, material inputs, labour, and depreciation of equipment), to define an expected profit-based objective function. Yields of intermediate products can be included in the objective function based on the effect each intermediate product yield has on the factors affecting expected profit (e.g., reduced material input costs for intermediate products used in the synthesis of a final product, storage costs for intermediate products, etc.).

The constraints 328 can define thresholds or other predefined limits on parameter values, and/or relationships between parameter values. The constraints 328 can be hard of soft constraints. Hard constraints can define hard limits for values of a given parameter, constraining the parameter space within which the LP solver must find a solution to the LP problem. Soft constraints, in some examples, can be encoded into the objective function 326 as non-linear or discontinuous terms in the objective function 326.

In some examples, the constraints 328 include one or more safety constraints, such as a maximum safe concentration of a chemical in certain stage of the hydrocarbon processing system 10 for avoiding unacceptable risk to personnel and/or equipment. In some examples, the safety constraints include a maximum gas pressure constraint for one or more stages, requiring the maintenance of a predicted pressure of at least one stage of the hydrocarbon processing system below a pressure threshold. For example, in some crude refineries, a crude feedstock batch 102 having a high concentration of naptha as detected from the NMR data 320 is likely to give rise to dangerously high gas pressures at certain naptha processing stages, such as the delayed coker unit 40, when the intermediate products of the crude feedstock batch 102 are processed at that stage. Thus, for example, the LP problem definition 324 can include a pressure constraint that requires that a predicted gas pressure parameter (which could be a process measurement 318 of the delayed coker unit 40) must be maintained below a pressure threshold. In order to satisfy this pressure constraint, the operating parameters 316 can be adjusted in various ways; e.g., by adjusting a flow rate and/or temperature of one or more stages upstream from the delayed coker unit 40, or by adjusting a valve position parameter of a gas release component in the delayed coker unit 40 to release excess pressure created by the predicted yield of coker naptha 144.

In some examples, the constraints 328 include a product supply constraint representative of a commitment to supply a committed quantity of a specific product, such as a final product. For example, if the operator of the hydrocarbon processing system 10 has supply contracts in place requiring the supply of a fixed quantity of volume of a specific final product, or of a final product having a specific set of characteristics (such as a specific gasoline blend blended at the gasoline blending pool 50), by a specific date, then a product supply constraint can be included in the LP problem definition 324 that requires the optimized operating parameter data 320 to result in production of at least the fixed quantity of the required product by the specific date (or in time to store and transport the product by the specific date). In some examples, the product supply is a soft constraint encoded in the objective function 326 as a set of discontinuous or non-linear terms: for example, if the supply contract dictates a minimum volume of fuel oil supplied by date D, a first revenue per barrel for fuel oil between the minimum volume and a maximum volume, a reduced second revenue per barrel for fuel oil over the maximum volume, and a penalty cost per barrel of fuel oil below the minimum volume, then these revenues and costs can be encoded into the objective function 326 as a soft constraint. In some examples, such a constraint can be implemented as a combination of hard and soft constraints: for example, the minimum volume of fuel oil can be represented as a hard constraint 328, with the two-tiered price per barrel (over the minimum volume, and over the maximum volume) encoded into the objective function.

Thus, in some embodiments, the operating parameters 316 of the hydrocarbon processing system 10, or of a sub-system or stage thereof, can be adjusted by the plant optimization software system 300 based on the optimized operating parameter data 330. In some embodiments, the optimized operating parameter data 330 is presented to an operator of the hydrocarbon processing system 10 via an output device, such as a user device 247 (e.g., a workstation with a display device). Details of an example user interface for interacting with the operator of the hydrocarbon processing system 10 are described below with reference to FIG. 6. Details of the co-operation of the plant optimization software system 300 with the hydrocarbon processing system 10 are described in detail below with reference to the method of FIG. 5.

In some examples, when the plant optimization software system 300 is operating in deployment mode, the actual product yields may be recorded and used for further training of the yield prediction model as additional yield data 340 in association with the corresponding yield prediction data 322 and the NMR data 320 and other inputs giving rise to the yield prediction data 322.

Figure 4:
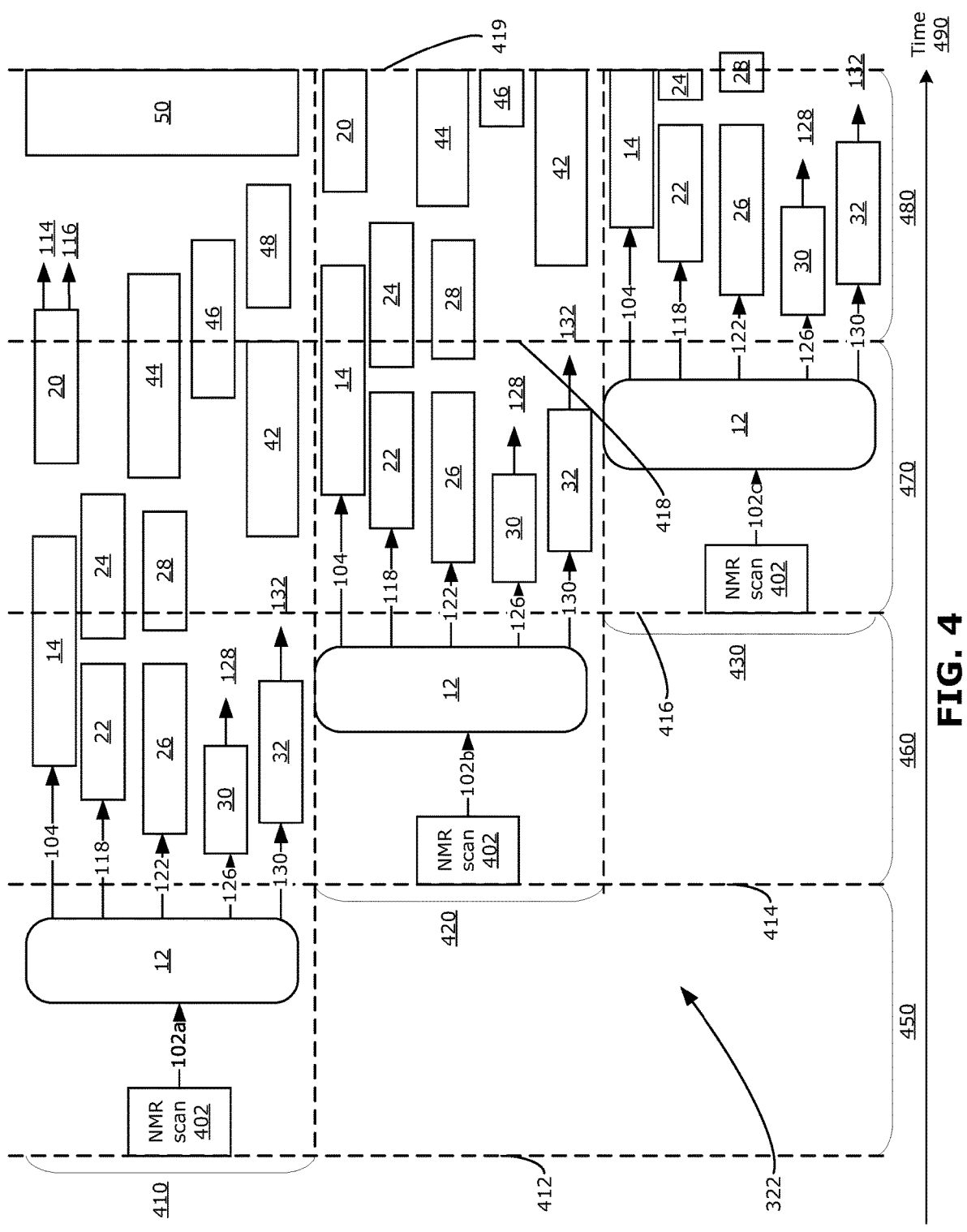

FIG. 4 shows an example of yield prediction data 322 generated over time 490 with respect to multiple batches of hydrocarbon feedstock material, such as crude batch 102. Three such batches of yield prediction data 322, each corresponding to a respective batch of hydrocarbon feedstock material, are shown as first yield prediction data batch 410 (corresponding to first batch of hydrocarbon feedstock material 102*a*), second yield prediction data batch 420 (corresponding to second batch of hydrocarbon feedstock material 102*b*), and third yield prediction data batch 430 (corresponding to third batch of hydrocarbon feedstock material 102*c*). In some examples, the hydrocarbon process-ing system 10 operates to perform a NMR scan (at NMR scanner 402) of a sample of an incoming batch of crude or other hydrocarbon feedstock material at regular intervals, such as every 20 minutes. These periodic NMR scans result in periodic batches of NMR data 320. The NMR data 320 can be processed by the plant optimization software system 300, operating in deployment mode, in real time to generate a corresponding batch of yield prediction data.

As used herein, the word "batch" can refer either to a portion of hydrocarbon feedstock material such as crude oil 102, or to a portion of data generated based on a batch of hydrocarbon feedstock material. For example, a batch of crude can refer to an amount of crude received by the hydrocarbon processing system 10 over a period of time, such as 20 minutes or some other period of time. A batch of yield prediction data 322 (such as first yield prediction data batch 410) can refer to a portion of yield prediction data 322 containing predictions for yields of various products at various stages of the hydrocarbon processing system 10 at times when those stages are expected to process a given batch of hydrocarbon feedstock material or intermediate products derived therefrom.

Thus, in the illustrated example, each batch of yield prediction data 410, 420, 430 is generated 20 minutes after the previous batch of data, and each such batch 410, 420, 430 corresponds to predicted product yields and/or or other predicted parameters pertaining to various stages in the hydrocarbon processing system 10 at differing time periods that correspond to a time at which the given stage is expected to be processing the hydrocarbon feedstock mate-rial (or intermediate products derived therefrom) that was the subject of the corresponding NMR data 320. The first yield prediction data batch 410 is generated based on an NMR scan performed at first time 412; the second yield prediction data batch 420 is generated based on an NMR scan performed at second time 414; the third yield prediction data batch 430 is generated based on an NMR scan per-formed at third time 416. Additional NMR scans, and corresponding batches of yield prediction data based on the NMR data 320 from those scans (not shown), can be performed at fourth time 418 and fifth time 419. Each time 412, 414, 416, 418, 419 is 20 minutes after the previous time in this example. The time periods between each pair of times 412, 414, 416, 418, 419 are shown as first time period 450, second time period 460, third time period 470, and fourth time period 480.

In each batch 410, 420, 430, the yield prediction data 322 generates predictions for various stages of the hydrocarbon processing system 10 pertaining to a time or a time period at which the stage is expected to process the corresponding feedstock material batch 102*a*, 102*b*, 102*c* or its derivatives (i.e., intermediate products derived therefrom). In some embodiments, a batch of hydrogen feedstock material makes its way through the various stages of the hydrocarbon processing system 10 according to a predictable time course, such that a given batch of yield prediction data 322, such as batch 410, predicts product yields for different stages at different times. As shown in the simplified example of FIG. 4, the first yield prediction data batch 410 includes yield prediction data 322 predicting product yields and/or other parameter values for the atmospheric distillation unit 12 during first time period 450; yield prediction data 322 for the hydrotreater units 22, 26, 32 and merox treater unit 30 during second time period 460; yield prediction data 322 for the FCC unit 42 during third time period 470; and yield prediction data 322 for the hydrotreater unit 48 during fourth time period 480.

This means, for example, that the first batch of hydrocar-bon feedstock material 102*a* is expected, based on the known operating history of the hydrocarbon processing system 10, to be processed by the atmospheric distillation unit 12 during a time period between 0 and 20 minutes from when the NMR scanner 402 scans the feedstock batch 102*a*, thereby yielding its products (i.e., gas 104, light naptha 118, heavy naptha 122, unrefined jet fuel or kerosene 126, wet diesel oil 130, atmospheric gas oil 134, and atmospheric bottoms 136) during the first time period 450 in volumes or at rates corresponding to the predictions of the first yield prediction data batch 410. Similarly, the yield prediction data 322 predicts that the FCC unit 42 will produce its products (i.e., butenes and pentenes 156, naptha 152, and FCC gas oil 148) during third time period 470 at rates or in volumes corresponding to the yield predictions of the first yield prediction data batch 410.

In some examples, as shown in FIG. 4, one or more stages (such as stages 14, 24, 28, 20, 44, and 46) will span more than one of the time periods 450, 460, 470, 480 and will therefore have their product yields for a given time period predicted by more than one batch of yield prediction data. In some examples, yield prediction data 322 from multiple yield prediction data batches can be combined, for example as a weighted average, to predict the product yields or other parameters of such stages. In some embodiments, each stage has its own distinct time period defined in the yield predic-tion data, such as a distinct time period corresponding to the horizontal span occupied by the stage in FIG. 4 with respect to time axis 490. In some examples, the yield prediction data 322 predicts a more detailed time course of product yields, such that a flow rate of each product is predicted at each of multiple points in time within the relevant time period.

Each subsequent batch of yield prediction data follows the same time course, offset by the delay between NMR scans. Thus, after multiple batches of yield prediction data have been generated, the yield prediction data 322 includes predictions for product yields for all stages during the current time period as well as all future time periods through the end of the time course of the most recent batch of yield prediction data. In some embodiments, this enables the optimization module 304 to optimize operation of the hydrocarbon processing system 10 based on the combined predicted time courses over all stages over all such time periods. Such optimization is referred to herein as "end to end optimization". By adjusting the operating parameters affecting operation of all stages during the current and all future time periods, the optimization module 304 can leverage all of the NMR data 320 and yield prediction data 322 at its disposal to optimize the objective function 326 and satisfy the constraints 328.

In some examples, the time course dictating the relationship between the various stages and the time periods may be modified based on adjustments to the operating parameters and/or other parameters (such as feedstock characteristics). For example, a dwell time or flow rate of a given product at or through a given stage can be dictated at least in part by the values of the operating parameters 316. Thus, when the operating parameters 316 are adjusted in accordance with the optimized operating parameter data 330, the time period for one or more stages can change. In some examples, this change is reflected in the distinct time period designated in the yield prediction data 322 as being the time period to which that stage's predictions apply.

FIG. 5 is flowchart showing operations of a method 500 for optimizing the end to end operation of a hydrocarbon processing system using nuclear magnetic resonance spectroscopy data. The method 500 will be described in the context of the example hydrocarbon processing system 10, configured as a crude refinery, processing crude oil 102, using a computing system 240 executing the plant optimization software system 300. However, it will be appreciated that the operations or steps of method 500 are not limited to this example and can be implemented using other hydrocarbon processing systems, processing other hydrocarbon feedstock materials, using other software systems executed by other computing systems, etc.

At 502, a batch of crude 102 (e.g., first batch 102a) is received by the hydrocarbon processing system 10 and a sample of the crude is scanned by the NMR scanner 402. The NMR data 320 is generated based on the results of the NMR scan, as described above.

At 504, the NMR data 320 is processed by the yield prediction model 302 to generate a batch of yield prediction data 322, as described above. In some examples, the yield prediction model 302 also processes other parameters, such as process characteristics (i.e. process measurements 318 and operating parameters 316) and/or feedstock characteristics 312. The batch of yield prediction data 322 can be combined with other yield prediction data batches generated with respect to different NMR scans at different times to generate temporally overlapping yield prediction data 322 with respect to different stages of the hydrocarbon processing system 10 at various time periods, as described above with reference to FIG. 4.

At 506, the yield prediction data 322 is processed by the optimization module 304 to generate optimized operating parameter data 330, as described above. In some embodiments, step 506 includes steps 508, 510, and/or 512.

At 508, the optimization module 304 obtains multiple batches of yield prediction data 322 (e.g., batches 410, 420, and 430) in order to perform the optimization step 506. Having access to multiple batches of yield prediction data 322 enables end to end yield predictions across all stages of the hydrocarbon processing system 10 (also referred to herein as "end to end product yield data"), allowing the optimization module 304 to optimize current operating parameters 316 across all stages of the hydrocarbon processing system 10, i.e. to perform end to end optimization.

At 510, the optimization module 304 obtains the LP problem definition 324, as described above. The LP problem definition 324 can be retrieved from the memory 244 or another data source, where it is configured based on the preferences and priorities of the operator of the hydrocarbon processing system 10. In some examples, the LP problem definition 324 changes dynamically based on changing conditions, such as market prices, costs, time of day, current supply contracts, and so on.

At 512, the optimization module 304 uses the LP solver algorithm to solve the LP problem defined by the LP problem definition 324 to satisfy the constraints 328 and optimize or improve the objective function 326 relative to a baseline, e.g., relative to the objective function value assuming operation under the current process configuration. The LP solver can use multiple batches of yield prediction data 322, as described above with reference to step 508 and FIG. 4, to perform end to end optimization of the hydrocarbon processing system 10 by identifying an optimal set of operating parameter 316 values over the time course defined by the multiple overlapping batches of yield prediction data 322.

In some examples, the optimized operating parameter data 330 is provided to the yield prediction model 302 after step 506, to allow the yield prediction model 302 to generate a further set of yield prediction data 322 based on the operating parameter 316 values encoded in the optimized operating parameter data 330. In some examples, the operating parameters 316 are provided to the yield prediction model 302 only after the operating parameters 316 defining the process configuration have actually been adjusted based on the optimized operating parameter data 330 at step 514 below.

At 514, the operating parameters 316 defining the process configuration of the hydrocarbon processing system 10 are adjusted based on the optimized operating parameter data 330. For example, one or more flow rates, temperatures, dwell times, or valve positions of one or more stages of the hydrocarbon processing system 10 can be adjusted based on the optimized operating parameter data 330. In some embodiments, the optimized operating parameter data 330 or a portion thereof is presented to a human user or operator via a user interface, as described below with reference to FIG. 6, and the human user or operator provides user input electing to adopt some or all of the recommended adjustments of the optimized operating parameter data 330. In some embodiments, the optimized operating parameter data 330 is used to automatically adjust one or more of the operating parameters 316, for example via process controllers 249 (e.g., automatic valve actuators or heater controls). In some examples, the optimized operating parameter data 330 undergoes further processing before being implemented in the process configuration at step 514: for example, safety failsafe mechanisms can be used to prevent the operating parameters 316 to be set to unsafe values, thereby providing a further safety check in addition to any safety constraints included in the LP problem definition 324.

At 516, the hydrocarbon processing system 10 is operated, in accordance with the process configuration adjusted based on the optimized operating parameter data 330, to process the hydrocarbon feedstock material (e.g., crude 102) to generate the plurality of products. In some examples, step 516 includes one or more of steps 518 and/or 520.

At 518, the operating parameters 316 of the adjusted process configuration are set such that the hydrocarbon processing system 10 generates one or more desired product blends. For example, a gasoline blend can be modified as to any of its various component concentrations by adjusting the amounts of its various component intermediate products that are supplied to the gasoline blending pool 50 over a given time period.

At 520, to the extent that the adjusted operating parameters 316 change the expected delay between a given NMR scan and the processing of the scanned crude batch (e.g., first batch 102a) at a given stage of the hydrocarbon processing system 10, the yield prediction model 302 can change the time period definitions associated with that stage, as described above with reference to FIG. 4. In some examples, this modification to the time period definitions is implemented by computing additional parameter values, based on the adjusted operating parameters 316, that correspond to the expected delay, and providing these additional parameters as inputs to the yield prediction model 302.

Figure 6:
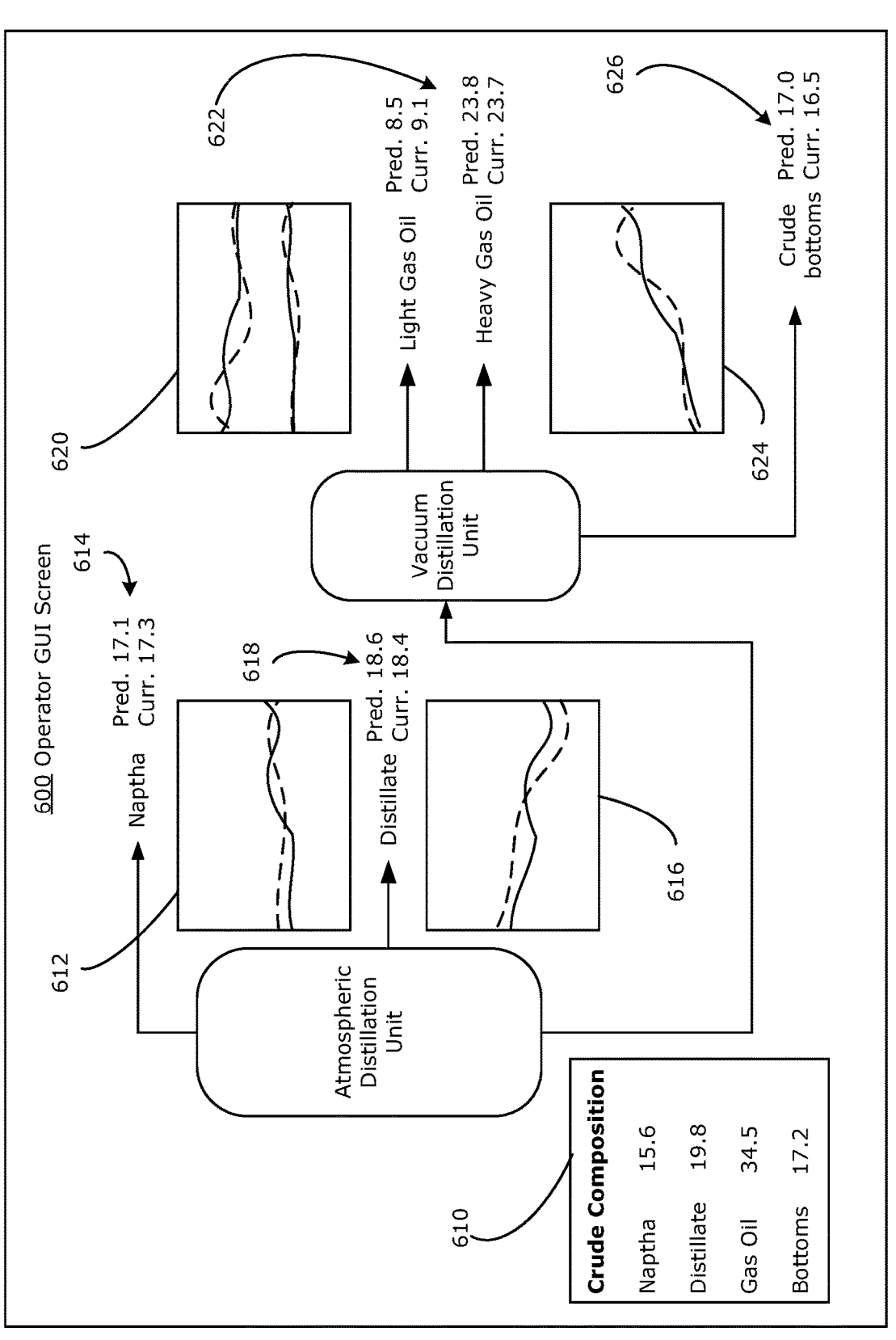
FIG. 6 is an example operator graphical user interface (GUI) screen, in accordance with example implementations described herein.

FIG. 6 shows an operator graphical user interface (GUI) screen 600. The operator GUI screen 600 can be displayed to an operator of the hydrocarbon processing system 10 via a user output device (i.e. a user device 247) such as a display, thereby enabling an operator of the hydrocarbon processing system 10 to monitor the yield prediction data graphed against current process measurements 318. Other GUI screens (not shown) can also be used in some embodiments to enable the operator to review, approve, and/or modify recommendations made by the optimization module 304, as described above with reference to step 514 of method 500.

The example operator GUI screen 600 shown in FIG. 6 includes a crude batch composition panel 610 showing a rough breakdown of the concentration of various components (e.g. 15.6% naptha, 19.8% distillate, and so on) of the most recently scanned crude batch 102, based on the NMR data 320 for the current crude batch 102. The various products generated by the atmospheric distillation unit 12 are monitored and displayed as various graphs and numerical readouts of both predicted and measured product yields.

A naptha graph 612 shows the predicted and currently measured levels of naptha products (e.g., combined yield of light naptha 118 and heavy naptha 122, divided by total product yields over all products, to generate a normalized percentage). The dashed line represents a time course of the predicted naptha product yield (based on product yield data 322 generated based on NMR data 320 obtained at the corresponding time delay in the past), and the solid line represents a time course of the measured naptha product yield actually being generated by the atmospheric distillation unit 12 (e.g., a process measurement 318 generated based on readings from sensors 248, such as flow rate sensors at naptha processing stages 22 and 26). The naptha graph 612 is displayed near a numerical naptha readout 614 of the predicted and measured naptha levels corresponding to the current time.

Similar graphs and numerical readouts are provided by the other products of the atmospheric distillation unit 12, and for the products of the vacuum distillation unit 34: a distillate graph 616 and distillate readout 618 (showing levels of distillate, e.g., wet jet fuel or kerosene 126 and wet diesel oil

130), a combined gas oil graph 620 and combined gas oil readout 622 (showing separate levels of light vacuum gas oil 138 and heavy vacuum gas oil 160), and a crude bottoms graph 624 and crude bottoms readout 626 (showing levels of vacuum residuum 141). Some of the graphs can include separate time course graphs for separate products, such as the illustrated combined gas oil graph 620, which shows predicted and measured levels for light gas oil and, separately, for heavy gas oil. Similarly, some of the numerical readouts include numerical concentrations of multiple separate products, such as the illustrated combined gas oil readout 622, which shows numerical values for the predicted and measured levels of both light oil and, separately, heavy gas oil at the current time.

Although the illustrated example GUI screen 600 shows all numerical values in terms of normalized concentrations, in order to allow comparison of each numerical value to the values shown in the crude composition panel 610, some examples may display and/or graph product levels as yields (such as volumetric flow rates) or another measure of quantity.

General

Although the present disclosure describes functions performed by certain components and physical entities, it should be understood that, in a distributed system, some or all of the processes can be distributed among multiple components and entities, and multiple instances of the processes can be carried out over the distributed system.

Although the present disclosure describes methods and processes with steps in a certain order, one or more steps of the methods and processes can be omitted or altered as appropriate. One or more steps can take place in an order other than that in which they are described, as appropriate.

Although the present disclosure is described, at least in part, in terms of methods, a person of ordinary skill in the art will understand that the present disclosure is also directed to the various components for performing at least some of the aspects and features of the described methods, either by way of hardware components, software or any combination of the two. Accordingly, the technical solution of the present disclosure can be embodied in the form of a software product. A suitable software product can be stored in a pre-recorded storage device or other similar non-volatile or non-transitory computer readable medium, including DVDs, CD-ROMs, USB flash disk, a removable hard disk, or other storage media, for example. The software product includes instructions tangibly stored thereon that enable a processing device (e.g., a personal computer, a server, or a network device) to execute examples of the methods disclosed herein. In general, the software improves the operation of the hardware in one or more ways.

The present disclosure can be embodied in other specific forms without departing from the subject matter of the claims. The described example implementations are to be considered in all respects as being only illustrative and not restrictive. Selected features from one or more of the above-described implementations can be combined to create alternative implementations not explicitly described, features suitable for such combinations being understood within the scope of this disclosure.

All values and sub-ranges within disclosed ranges are also disclosed. Also, although the systems, devices and processes disclosed and shown herein can include a specific number of elements/components, the systems, devices and assemblies could be modified to include additional or fewer of such elements/components. For example, although any of the elements/components disclosed can be referenced as being singular, the implementations disclosed herein could be modified to include a plurality of such elements/components. The subject matter described herein intends to cover and embrace all suitable changes in technology.

The invention claimed is:

1. A method comprising:

performing a nuclear magnetic resonance (NMR) scan of a sample of a hydrocarbon feedstock material to generate NMR data;

processing the NMR data, using a yield prediction model, to generate yield prediction data, the yield prediction data including a predicted yield for each of a plurality of products resulting from the processing of the hydrocarbon feedstock material by a hydrocarbon processing system; and adjusting one or more operating parameters defining a process configuration of the hydrocarbon processing system based on the yield prediction data, wherein the yield prediction data includes, for each respective stage of a plurality of stages of the hydrocarbon processing system, a predicted yield of at least one respective product at a respective time period, such that the respective time period corresponds to a time at which the hydrocarbon feedstock material or materials derived from the hydrocarbon feedstock material are being processed by the respective stage.

2. The method of claim 1, wherein:

the hydrocarbon feedstock material comprises crude oil; and the plurality of products includes at least one of the following:

a naphtha product, a distillate product, a gas oil product, a crude bottom product, a light vacuum gas oil product, a heavy vacuum gas oil product, and a coker feed product.

3. The method of claim 2, wherein:

the plurality of products comprises a naphtha product; and the method further comprises adjusting one or more operating parameters of the process configuration, based on the yield prediction data, to maintain a predicted pressure of at least one stage of the hydrocarbon processing system below a pressure threshold.

4. The method of claim 1, further comprising:

repeating, for one or more batches of hydrocarbon feedstock material, the steps of performing the NMR scan and generating the yield prediction data, such that yield prediction data is obtained for a plurality of batches of hydrocarbon feedstock material;

processing the yield prediction data for the plurality of batches of hydrocarbon feedstock material to determine end to end product yield data comprising predicted yields for at least one product over at least one time period for each stage; and adjusting one or more operating parameters of the process configuration based on the end to end product yield data.

5. The method of claim 4, wherein adjusting the one or more operating parameters of the hydrocarbon processing system based on the end to end product yield data comprises:

obtaining a linear programming (LP) problem definition comprising an objective function;

processing the end to end product yield data, using an optimization module comprising an LP problem solver, to solve a LP problem defined by the LP problem definition, thereby generating optimized operating parameter data comprising one or more values for the operating parameters corresponding to a desired value for the objective function; and adjusting the one or more operating parameters based on the optimized operating parameter data.

6. The method of claim 5, wherein:

the objective function includes a plurality of terms corresponding to market prices for a plurality of final products producible by the hydrocarbon processing system.

7. The method of claim 5, wherein:

the LP problem definition further comprises one or more constraints.

8. The method of claim 7, wherein:

the one or more constraints includes a pressure constraint representative of maintaining a pressure value below a pressure threshold at a naptha processing stage of the hydrocarbon processing system; and the pressure value is predicted based on a predicted rate of production of a naptha product of the yield prediction data.

9. The method of claim 8, wherein adjusting the one or more operating parameters based on the optimized operating parameter data comprises:

adjusting the one or more operating parameters to maintain the pressure value below the pressure threshold at the naptha processing stage.

10. The method of claim 7, wherein:

the one or more constraints includes a product supply constraint representative of a commitment to supply a committed quantity of a first product.

11. The method of claim 1, wherein:

the operating parameters include one or more parameters representative of at least one of the following:

a temperature;

a flow rate;

a dwell time; and a valve position.

12. The method of claim 1, further comprising, after adjusting the operating parameters defining the process configuration:

processing the hydrocarbon feedstock material, using the hydrocarbon processing system configured in accordance with the process configuration, to generate the plurality of products.

13. The method of claim 1, wherein:

the yield prediction model generates the yield prediction data by processing the NMR data and one or more additional parameters;

the one or more additional parameters comprise at least one of the following:

one or more process characteristics representative of characteristics of the hydrocarbon processing system; and one or more feedstock characteristics representative of characteristics of the hydrocarbon feedstock material.

14. The method of claim 1, wherein:

the yield prediction model is a machine learning model trained using supervised learning based on training data comprising:

NMR data for a plurality of hydrocarbon feedstock material batches; and yield data representative of, for each hydrocarbon feedstock material batch, a plurality of product yields generated by processing the hydrocarbon feedstock material batch via the hydrocarbon processing system.

15. The method of claim 1, wherein:

the yield prediction model is a statistical model generated based on statistical correlations between:

NMR data for a plurality of hydrocarbon feedstock material batches; and yield data representative of, for each hydrocarbon feedstock material batch, a plurality of product yields generated by processing the hydrocarbon feedstock material batch via the hydrocarbon processing system.

16. The method of claim 1, wherein:

the NMR data comprises a NMR fingerprint.

17. The method of claim 1, wherein:

the NMR data is representative of a composition of the sample, comprising a plurality of components each associated with a respective concentration.

18. A system, comprising:

a nuclear magnetic resonance (NMR) spectroscopy scanner for performing NMR scans of hydrocarbon feedstock material;

a processor device; and a memory storing instructions that, when executed by the processor device, cause the system to perform a method as claimed in claim 1.

19. A non-transitory computer-readable medium storing instructions thereon to be executed by a processor device, the instructions, when executed, causing the processor device to perform a method as claimed in claim 1.

20. A method comprising:

performing a nuclear magnetic resonance (NMR) scan of a sample of a hydrocarbon feedstock material to generate NMR data; and processing the NMR data, using a yield prediction model, to generate yield prediction data, the yield prediction data including a predicted yield for each of a plurality of products resulting from the processing of the hydrocarbon feedstock material by a hydrocarbon processing system;

wherein:

(i) the yield prediction model is a machine learning model trained using supervised learning based on training data comprising:

NMR data for a plurality of hydrocarbon feedstock material batches; and yield data representative of, for each hydrocarbon feedstock material batch, a plurality of product yields generated by processing the hydrocarbon feedstock material batch via the hydrocarbon processing system; or (ii) the yield prediction model is a statistical model generated based on statistical correlations between:

NMR data for a plurality of hydrocarbon feedstock material batches; and yield data representative of, for each hydrocarbon feedstock material batch, a plurality of product yields generated by processing the hydrocarbon feedstock material batch via the hydrocarbon processing system.

21. A method comprising:

performing a nuclear magnetic resonance (NMR) scan of a sample of a hydrocarbon feedstock material to generate NMR data; and processing the NMR data, using a yield prediction model, to generate yield prediction data, the yield prediction data including a predicted yield for each of a plurality of products resulting from the processing of the hydrocarbon feedstock material by a hydrocarbon processing system, wherein the NMR data comprises a NMR fingerprint.

* * * * *